US009814767B2

(12) United States Patent
Knutson et al.

(10) Patent No.: US 9,814,767 B2
(45) Date of Patent: Nov. 14, 2017

(54) METHODS AND MATERIALS FOR GENERATING CD8+ T CELLS HAVING THE ABILITY TO RECOGNIZE CANCER CELLS EXPRESSING A HER2/NEU POLYPEPTIDE

(71) Applicant: Mayo Foundation for Medical Education and Research, Rochester, MN (US)

(72) Inventors: Keith L. Knutson, Fort Pierce, FL (US); Andrea M. Henle, Cambridge, MA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 302 days.

(21) Appl. No.: 14/379,150

(22) PCT Filed: Feb. 15, 2013

(86) PCT No.: PCT/US2013/026484
§ 371 (c)(1),
(2) Date: Aug. 15, 2014

(87) PCT Pub. No.: WO2013/123424
PCT Pub. Date: Aug. 22, 2013

(65) Prior Publication Data
US 2015/0231218 A1   Aug. 20, 2015

Related U.S. Application Data

(60) Provisional application No. 61/600,480, filed on Feb. 17, 2012.

(51) Int. Cl.
*A61K 39/00* (2006.01)
*A61K 39/36* (2006.01)
*C07K 7/06* (2006.01)
*C07K 14/71* (2006.01)
*A61K 45/06* (2006.01)

(52) U.S. Cl.
CPC .......... *A61K 39/0011* (2013.01); *A61K 45/06* (2013.01); *C07K 14/71* (2013.01); *A61K 2039/55566* (2013.01)

(58) Field of Classification Search
None
See application file for complete search history.

(56) References Cited

U.S. PATENT DOCUMENTS

| 4,237,224 A | 12/1980 | Cohen et al. |
| 4,273,875 A | 6/1981 | Manis |
| 4,363,877 A | 12/1982 | Goodman et al. |
| 4,428,941 A | 1/1984 | Galibert et al. |
| 4,431,739 A | 2/1984 | Riggs |
| 5,595,756 A * | 1/1997 | Bally .................. A61K 9/1272 264/4.1 |
| 5,846,538 A | 12/1998 | Cheever et al. |
| 6,514,942 B1 | 2/2003 | Ioannides et al. |
| 7,807,441 B2 | 10/2010 | Steinaa et al. |
| 8,858,952 B2 | 10/2014 | Knutson |
| 2002/0055614 A1* | 5/2002 | Cheever ............. A61K 39/0011 530/300 |
| 2005/0169934 A1 | 8/2005 | Ioannides et al. |
| 2010/0209443 A1 | 8/2010 | People's et al. |
| 2010/0310640 A1 | 12/2010 | Knutson et al. |
| 2014/0377340 A1 | 12/2014 | Knutson et al. |

FOREIGN PATENT DOCUMENTS

| WO | WO9961916 A1 | 12/1999 |
| WO | WO0141787 | 6/2001 |

OTHER PUBLICATIONS

Baxevanis et al. Immunotherapy, 2010:213-26.*
Lollini et al. Nature Review Cancer. Mar. 2006;6(3):204-16.*
Heppner et al. Cancer Metastasis Review 2:5-23; 1983.*
Jain RK. Scientific American, Jul. 1994, 58-65.*
Knutson et al. Immunization of Cancer Patients with a HER-2/neu, HLA-A2 Peptide, p. 369-377, Results in Short-lived Peptide-specific Immunity. Clinical Cancer Research, 2002; 8:1014-1018.*
Clinical trial NCT01355393, May 16, 2011.*
Repka et al. Trastuzumab and Interleukin-2 in HER2-positive Metastatic Breast Cancer: A Pilot Study1. Clinical Cancer Research, 2003; 9: 2440-2446.*
Norell et al. Vaccination with a plasmid DNA encoding HER-2/neu together with low doses of GM-CSF and IL-2 in patients with metastatic breast carcinoma: a pilot clinical trial. Journal of Translational Medicine, 2010; 8:53.*
Tugues et al. New insights into IL-12-mediated tumor suppression. Cell Death and Differentiation, 2015; 2:237-246.*
Henle et al., "Enzymatic discovery of a HER-2/neu epitope that generates cross-reactive T cells," J Immunol., 190(1):479-488, Epub Nov. 23, 2012.
Henle et al., "Identification of HER-2/neu peptide p373-382 as a naturally processed immunodominant HLA-A2 binding epitope," J Immunol, 188 (Meeting Abstract Supplement) Abstract 46.11 , 1 page, May 2012.
Knutson et al., "Immunization of cancer patients with a HER-2/neu, HLA-A2 peptide, p369-377, results in short-lived peptide-specific immunity," Clin Cancer Res., 8(5):1014-1018, May 2002.
European Search Report for App. No. 13749730, dated Aug. 13, 2015, 10 pages.
Aucouturier et al., "Adjuvants designed for veterinary and human vaccines," Vaccine, 19(17-19):2666-2672, Mar. 21, 2001.
Fisk et al., "Identification of an immunodominant peptide of HER-2/neu protooncogene recognized by ovarian tumor-specific cytotoxic T lymphocyte lines," J Exp Med., 181(6):2109-2117, Jun. 1, 1995.

(Continued)

*Primary Examiner* — Vanessa L Ford
*Assistant Examiner* — Sandra Dillahunt
(74) *Attorney, Agent, or Firm* — Fish & Richardson P.C.

(57) ABSTRACT

This document provides methods and materials for generating CD8+ T cells having the ability to recognize cancer cells expressing a HER2/neu polypeptide. For example, methods and materials for using a polypeptide consisting of an SLAFLPESFD amino acid sequence in vivo or in vitro to generate CD8+ T cells having the ability to recognize and lyse cancer cells expressing a HER2/neu polypeptide are provided.

15 Claims, 6 Drawing Sheets

(56) References Cited

OTHER PUBLICATIONS

Gritzapis et al., "HER-2/neu (657-665) represents an immunogenic epitope of HER-2/neu oncoprotein with potent antitumor properties," Vaccine., 28(1):162-170, Epub Sep. 30, 2009.

Holmes et al., "Results of the first phase I clinical trial of the novel II—key hybrid preventive HER-2/neu peptide (AE37) vaccine," J Clin Oncol., 26(20):3426-3433, Jul. 10, 2008.

Karyampudi et al., "A degenerate HLA-DR epitope pool of HER-2/neu reveals a novel in vivo immunodominant epitope, HER-2/neu88-102," Clin Cancer Res., 16(3):825-834, Epub Jan. 26, 2010.

Knutson and Disis, "Clonal diversity of the T-cell population responding to a dominant HLA-A2 epitope of HER-2/neu after active immunization in an ovarian cancer patient," Hum Immunol., 63(7):547-557, Jul. 2002.

Knutson et al., "Immunization with a HER-2/neu helper peptide vaccine generates HER-2/neu CD8 T-cell immunity in cancer patients," J Clin Invest., 107(4):477-484, Feb. 2001.

Perez et al., "HER-2/neu-derived peptide 884-899 is expressed by human breast, colorectal and pancreatic adenocarcinomas and is recognized by in-vitro-induced specific CD4(+) T cell clones," Cancer Immunol Immunother., 50(11):615-624, Epub Nov. 23, 2001.

Salazar et al., "Immunization of cancer patients with HER-2/neu-derived peptides demonstrating high-affinity binding to multiple class II alleles," Clin Cancer Res., 9(15):5559-5565, Nov. 15, 2003.

Santin et al., "Trastuzumab treatment in patients with advanced or recurrent endometrial carcinoma overexpressing HER2/neu," Int J Gynaecol Obstet., 102(2):128-131, Epub Jun. 16, 2008.

Tam et al., "An SN2 deprotection of synthetic peptides with a low concentration of hydrofluoric acid in dimethyl sulfide: evidence and application in peptide synthesis," J. Am. Chem. Soc., 105(21):6442-6455, 1983.

Zaks and Rosenberg, "Immunization with a peptide epitope (p369-377) from HER-2/neu leads to peptide-specific cytotoxic T lymphocytes that fail to recognize HER-2/neu+ tumors," Cancer Res., 58(21):4902-4908, Nov. 1, 1998.

International Search Report and Written Opinion for PCT/US2013/026484, dated Jun. 6, 2013, 5 pages.

International Preliminary Report on Patentability for PCT/US2013/026484 dated Aug. 19, 2014, 4 pages.

Office Action in Chinese Application No. 201380019913.1, dated Mar. 25, 2016, 15 pages [English translation].

\* cited by examiner

SEQUENCE LISTING

<160> NUMBER OF SEQ ID NOS: 22

<210> SEQ ID NO 1
<211> LENGTH: 10
<212> TYPE: PRT
<213> ORGANISM: homo sapiens

<400> SEQUENCE: 1

Ser Leu Ala Phe Leu Pro Glu Ser Phe Asp
1               5                   10

<210> SEQ ID NO 2
<211> LENGTH: 9
<212> TYPE: PRT
<213> ORGANISM: homo sapiens

<400> SEQUENCE: 2

Lys Ile Phe Gly Ser Leu Ala Phe Leu
1               5

<210> SEQ ID NO 3
<211> LENGTH: 19
<212> TYPE: PRT
<213> ORGANISM: homo sapiens

<400> SEQUENCE: 3

Phe Ala Gly Cys Lys Lys Ile Phe Gly Ser Leu Ala Phe Leu Pro Glu
1               5                   10                  15

Ser Phe Asp

<210> SEQ ID NO 4
<211> LENGTH: 11

```
<212> TYPE: PRT
<213> ORGANISM: homo sapiens

<400> SEQUENCE: 4

Phe Gly Ser Leu Ala Phe Leu Pro Glu Ser Phe
1               5                   10

<210> SEQ ID NO 5
<211> LENGTH: 11
<212> TYPE: PRT
<213> ORGANISM: homo sapiens

<400> SEQUENCE: 5

Phe Ala Gly Cys Lys Lys Ile Phe Gly Ser Leu
1               5                   10

<210> SEQ ID NO 6
<211> LENGTH: 11
<212> TYPE: PRT
<213> ORGANISM: homo sapiens

<400> SEQUENCE: 6

Gly Ser Leu Ala Phe Leu Pro Glu Ser Phe Asp
1               5                   10

<210> SEQ ID NO 7
<211> LENGTH: 10
<212> TYPE: PRT
<213> ORGANISM: homo sapiens

<400> SEQUENCE: 7

Phe Gly Ser Leu Ala Phe Leu Pro Glu Ser
1               5                   10

<210> SEQ ID NO 8
<211> LENGTH: 10
<212> TYPE: PRT
<213> ORGANISM: homo sapiens

<400> SEQUENCE: 8

Gly Ser Leu Ala Phe Leu Pro Glu Ser Phe
1               5                   10

<210> SEQ ID NO 9
<211> LENGTH: 10
<212> TYPE: PRT
<213> ORGANISM: homo sapiens

<400> SEQUENCE: 9

Phe Ala Gly Cys Lys Lys Ile Phe Gly Ser
1               5                   10

<210> SEQ ID NO 10
<211> LENGTH: 9
<212> TYPE: PRT
<213> ORGANISM: homo sapiens

<400> SEQUENCE: 10

Leu Ala Phe Leu Pro Glu Ser Phe Asp
1               5

<210> SEQ ID NO 11
<211> LENGTH: 9
<212> TYPE: PRT
<213> ORGANISM: homo sapiens
```

```
<400> SEQUENCE: 11

Ser Leu Ala Phe Leu Pro Glu Ser Phe
 1               5

<210> SEQ ID NO 12
<211> LENGTH: 8
<212> TYPE: PRT
<213> ORGANISM: homo sapiens

<400> SEQUENCE: 12

Ala Phe Leu Pro Glu Ser Phe Asp
 1               5

<210> SEQ ID NO 13
<211> LENGTH: 19
<212> TYPE: PRT
<213> ORGANISM: Artificial Sequence
<220> FEATURE:
<223> OTHER INFORMATION: NH2 C-terminus

<400> SEQUENCE: 13

Phe Ala Gly Cys Lys Lys Ile Phe Gly Ser Leu Ala Phe Leu Pro Glu
 1               5                  10                  15

Ser Phe Asp

<210> SEQ ID NO 14
<211> LENGTH: 19
<212> TYPE: PRT
<213> ORGANISM: Artificial Sequence
<220> FEATURE:
<223> OTHER INFORMATION: COOH C-terminus

<400> SEQUENCE: 14

Phe Ala Gly Cys Lys Lys Ile Phe Gly Ser Leu Ala Phe Leu Pro Glu
 1               5                  10                  15

Ser Phe Asp

<210> SEQ ID NO 15
<211> LENGTH: 18
<212> TYPE: PRT
<213> ORGANISM: Artificial Sequence
<220> FEATURE:
<223> OTHER INFORMATION: NH2 C-terminus

<400> SEQUENCE: 15

Phe Ala Gly Lys Lys Ile Phe Gly Ser Leu Ala Phe Leu Pro Glu Ser
 1               5                  10                  15

Phe Asp

<210> SEQ ID NO 16
<211> LENGTH: 18
<212> TYPE: PRT
<213> ORGANISM: Artificial Sequence
<220> FEATURE:
<223> OTHER INFORMATION: COOH C-terminus

<400> SEQUENCE: 16

Phe Ala Gly Lys Lys Ile Phe Gly Ser Leu Ala Phe Leu Pro Glu Ser
 1               5                  10                  15

Phe Asp

<210> SEQ ID NO 17
```

```
<211> LENGTH: 10
<212> TYPE: PRT
<213> ORGANISM: homo sapiens

<400> SEQUENCE: 17

Phe Ala Gly Lys Lys Ile Phe Gly Ser Leu
1               5                   10

<210> SEQ ID NO 18
<211> LENGTH: 10
<212> TYPE: PRT
<213> ORGANISM: homo sapiens

<400> SEQUENCE: 18

Gly Lys Lys Ile Phe Gly Ser Leu Ala Phe
1               5                   10

<210> SEQ ID NO 19
<211> LENGTH: 8
<212> TYPE: PRT
<213> ORGANISM: homo sapiens

<400> SEQUENCE: 19

Leu Ala Phe Leu Pro Glu Ser Phe
1               5

<210> SEQ ID NO 20
<211> LENGTH: 9
<212> TYPE: PRT
<213> ORGANISM: influenza virus

<400> SEQUENCE: 20

Gly Ile Leu Gly Phe Val Phe Thr Leu
1               5

<210> SEQ ID NO 21
<211> LENGTH: 8
<212> TYPE: PRT
<213> ORGANISM: Homo sapiens

<400> SEQUENCE: 21

Leu Ala Phe Leu Pro Glu Ser Phe
1               5

<210> SEQ ID NO 22
<211> LENGTH: 8
<212> TYPE: PRT
<213> ORGANISM: Homo sapiens

<400> SEQUENCE: 22

Ser Leu Ala Phe Leu Pro Glu Ser
1               5
```

METHODS AND MATERIALS FOR GENERATING CD8+ T CELLS HAVING THE ABILITY TO RECOGNIZE CANCER CELLS EXPRESSING A HER2/NEU POLYPEPTIDE

CROSS-REFERENCE TO RELATED APPLICATIONS

This application is a National Stage application under 35 U.S.C. §371 of International Application No. PCT/US2013/026484, having an International Filing Date of Feb. 15, 2013, which claims the benefit of U.S. Provisional Application Ser. No. 61/600,480, filed Feb. 17, 2012. The disclosure of the prior application is considered part of (and is incorporated by reference in) the disclosure of this application.

STATEMENT AS TO FEDERALLY SPONSORED RESEARCH

This invention was made with government support under CA113861 awarded by the National Institutes of Health. The government has certain rights in the invention.

BACKGROUND

1. Technical Field

This document relates to methods and materials for generating CD8+ T cells having the ability to recognize cancer cells expressing a HER2/neu polypeptide. For example, this document relates to methods and materials for using a polypeptide consisting of an SLAFLPESFD amino acid sequence in vivo or in vitro to generate CD8+ T cells having the ability to recognize cancer cells expressing a HER2/neu polypeptide.

2. Background Information

Cancer vaccines have the ability to stimulate or restore the immune system so that it can fight cancer. In some cases, cancer vaccines can be designed to treat an existing cancer by strengthening the patient's defenses against the cancer.

SUMMARY

This document provides methods and materials for generating CD8+ T cells having the ability to recognize cancer cells expressing a HER2/neu polypeptide. For example, this document provides methods and materials for using a polypeptide consisting of an SLAFLPESFD amino acid sequence (SEQ ID NO:1) in vivo or in vitro to generate CD8+ T cells having the ability to recognize and lyse cancer cells expressing a HER2/neu polypeptide. A polypeptide consisting of an SLAFLPESFD amino acid sequence can be referred to as the SLAFLPESFD polypeptide, the p373-382 polypeptide, or a polypeptide consisting of the amino acid sequence set forth in SEQ ID NO:1. As described herein, the SLAFLPESFD polypeptide or a vaccine composition containing the SLAFLPESFD polypeptide can be administered to a cancer patient having cancer cells that express a HER2/neu polypeptide under conditions wherein the patient produces CD8+ T cells having the ability to recognize and lyse those cancer cells. In some cases, such CD8+ T cells can be referred to as CD8+ T cells generated using the SLAFLPESFD polypeptide.

Having the ability to generate CD8+ T cells with the ability to recognize and lyse cancer cells that express a HER2/neu polypeptide can allow clinicians to provide cancer patients with additional effective treatment options. For example, the vaccines provided herein can be used alone or in combination with other cancer treatment options to provide cancer patients with an effective population of CD8+ T cells designed to kill cancer cells that express a HER2/neu polypeptide.

In general, one aspect of this document features a polypeptide (e.g., a purified polypeptide), wherein the sequence of the polypeptide consists of the amino acid sequence set forth in SEQ ID NO:1. In some case, the polypeptide can include an N and/or C terminal modification.

In another aspect, this document features a vaccine composition comprising, or consisting essentially of, a polypeptide (e.g., a purified polypeptide), wherein the sequence of the polypeptide consists of the amino acid sequence set forth in SEQ ID NO:1. In some case, the polypeptide can include an N and/or C terminal modification. The composition can comprise an adjuvant. The adjuvant can be an oil and water mixture. The adjuvant can be Montanide ISA-51. The composition can comprise IL-2, IL-12, GM-CSF, or rintatolimod.

In another aspect, this document features a method for increasing the number of CD8+ T cells having the ability to kill cancer cells expressing a HER2/neu polypeptide. The method comprises, or consists essentially of, contacting a population of CD8+ T cells with a polypeptide (e.g., a purified polypeptide), wherein the sequence of the polypeptide consists of the amino acid sequence set forth in SEQ ID NO:1. The contacting step can occur in an ex vivo manner. The contacting step can occur in an in vivo manner.

In another aspect, this document features a method for increasing, within a human, the number of CD8+ T cells having the ability to kill cancer cells expressing a HER2/neu polypeptide. The method comprises, or consists essentially of, administering a vaccine composition to the human, wherein the composition comprises, or consists essentially of, a polypeptide (e.g., a purified polypeptide), wherein the sequence of the polypeptide consists of the amino acid sequence set forth in SEQ ID NO:1. In some case, the polypeptide can include an N and/or C terminal modification. The human can contain cancer cells expressing the HER2/neu polypeptide. The composition can comprise an adjuvant. The adjuvant can be an oil and water mixture. The adjuvant can be Montanide ISA-51. The composition can comprise IL-2, IL-12, GM-CSF, or rintatolimod. The method can comprise administering IL-2, IL-12, GM-CSF, rintatolimod, or a combination thereof to the human. The method can further comprise administering trastuzumab to the human.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 4B: anti-HLA-ABC).

FIG. 4D: anti-HLA-ABC).

DETAILED DESCRIPTION

This document provides methods and materials for generating CD8+ T cells having the ability to recognize cancer cells expressing a HER2/neu polypeptide. For example, this document provides methods and materials for using a polypeptide consisting of the amino acid sequence set forth in SEQ ID NO:1 in vivo or in vitro to generate CD8+ T cells having the ability to recognize and lyse cancer cells expressing a HER2/neu polypeptide. In some cases, this document provides the SLAFLPESFD polypeptide and vaccine compositions containing the SLAFLPESFD polypeptide as well as methods for using the SLAFLPESFD polypeptide or vaccine compositions containing the SLAFLPESFD polypeptide to generate CD8+ T cells having the ability to recognize cancer cells expressing a HER2/neu polypeptide.

In some cases, a polypeptide provided herein (e.g., a polypeptide consisting of the amino acid sequence set forth in SEQ ID NO:1) can be used in combination with dendritic cells to treat cancer. For example, dendritic cells contacted with the SLAFLPESFD polypeptide can be used to treat cancer.

The SLAFLPESFD polypeptide provided herein can be substantially pure. The term "substantially pure" with respect to a polypeptide refers to a polypeptide that has been separated from cellular components with which it is naturally accompanied. For example, a synthetically generated polypeptide can be a substantially pure polypeptide. Typically, a polypeptide provided herein is substantially pure when it is at least 60 percent (e.g., 65, 70, 75, 80, 90, 95, or 99 percent), by weight, free from proteins and naturally-occurring organic molecules with which it is naturally associated. In general, a substantially pure polypeptide will yield a single major band on a non-reducing polyacrylamide gel.

The SLAFLPESFD polypeptide provided herein can be prepared in a wide variety of ways. Because of its relatively short size, the SLAFLPESFD polypeptide can be synthesized in solution or on a solid automatic synthesizer in accordance with known protocols. See, for example, Stewart and Young, *Solid Phase Polypeptide Synthesis,* 2d. ed., Pierce Chemical Co. (1984); Tam et al., *J. Am. Chem. Soc.,* 105:6442 (1983); Merrifield, *The Polypeptides,* Gross and Meienhofer, ed., academic Press, New York, pp. 1-284 (1979). In some cases, a polypeptide provided herein (e.g., a SLAFLPESFD polypeptide) can be synthesized with either an amide (e.g., $NH_2$) or free acid (e.g., COOH) C terminus, both of which can have the ability to bind HLA-A2.

In some cases, recombinant DNA technology can be used wherein a nucleic acid sequence that encodes a SLAFLPESFD polypeptide provided herein is inserted into an expression vector, introduced (e.g., by transformation or transfection) into an appropriate host cell, and cultivated under conditions suitable for expression. These procedures are generally known in the art, as described generally in Sambrook et al., *Molecular Cloning, A Laboratory Manual,* Cold Spring Harbor Press, Cold Spring Harbor, N.Y. (1982), and Ausubel et al., (ed.) *Current Protocols in Molecular Biology,* John Wiley and Sons, Inc., New York (1987), and U.S. Pat. Nos. 4,237,224; 4,273,875; 4,431,739; 4,363,877; and 4,428,941, for example.

This document also provides polypeptides (e.g., substantially pure polypeptides) consisting of one of the amino acid sequences set forth in Table 1. Such polypeptides can be made and used in the same manner described herein for the SLAFLPESFD polypeptide.

In some cases, the polypeptides provided herein can be incubated with a population of CD8+ T cells to generate an activated pool of CD8+ T cells that have the ability to recognize p373-382 or a HER2/neu polypeptide. For example, one or more of the polypeptides provided herein (e.g., the SLAFLPESFD polypeptide) can be used in an ex vivo manner to created antigen-specific CD8+ T cells that can be used to treat cancers.

In some cases, the polypeptides provided herein can be used to generate a pool of activated HER2/neu polypeptide-specific CD8+ T cells that can be used alone, or in combination with monoclonal antibody therapy, CTL therapy, or both monoclonal antibody therapy and CTL therapy, to treat cancer. For example, an anti-HER-2/neu monoclonal antibody therapy can be combined with infusion of CD8+ T cells generated using p373-382 polypeptides to treat cancer (e.g., breast cancer). In some cases, a Herceptin (trastuzumab) therapy can be combined with infusion of CD8+ T cells generated using p373-382 polypeptides to treat cancer (e.g., breast cancer).

This document also provides vaccine compositions that contain an immunogenically effective amount of one or more of the polypeptides provided herein. A vaccine composition provided herein can be used both as a preventative or therapeutic vaccine. The vaccine compositions provided herein can be administered and formulated using any appropriate techniques including, without limitation, those techniques described elsewhere (see, e.g., [0132]-[0173] of U.S. Patent Application Publication No. 2010-0310640).

In some cases, a vaccine composition provided herein can include GM-CSF (e.g., sargramostim), rintatolimod (e.g., Ampligen®), IL-2, IL-12, an adjuvant, or a combination thereof. For example, a vaccine composition provided herein can include GM-CSF and an adjuvant. Examples of adjuvants include, without limitation, CpG oligonucleotides, monophosphoryl lipid A, and Montanide ISA-51. In some cases, the adjuvant can be an oil and water mixture such as Montanide ISA-51.

In some cases, a vaccine composition provided herein can include a combination of polypeptides. For example, a vaccine composition provided herein can include the SLAFLPESFD polypeptide and/or one or more of the other polypeptides set forth in Table 1 in combination with one or more polypeptides set forth in U.S. Patent Application Publication No. 2010-0310640, the Karyampudi et al. reference (*Clin. Cancer Res.*, 16(3):825-34 (2010)), the Holmes et al. reference (*J. Clin. Oncol.*, 26(20):3426-33 (2008)), the Gritzapis et al. reference (*Vaccine*, 28(1):162-70 (2009)), the Perez et al. reference (*Cancer Immunol. Immunother.*, 50(11):615-24 (2002)), the Knutson et al. reference (*J. Clin. Invest.*, 107(4):477-84 (2001)), or the Salazar et al. reference (*Clin. Cancer Res.*, 9(15):5559-65 (2003)).

Any appropriate method can be used to administer a vaccine composition provided herein to a mammal (e.g., a human). For example, a vaccine composition or polypeptide provided herein can be administered alone or in combination with other polypeptides in doses ranging from 100 to 10,000 micrograms given by intradermal or subcutaneous routes monthly for a total of four to twelve months (e.g., 4, 5, 6, 7, 8, 9, 10, 11, or 12 months).

The methods and materials provided herein can be used to treat any type of cancer that expresses a HER2/neu polypeptide. For example, the methods and materials provided herein can be used to treat breast cancer, ovarian cancer, colon cancer, esophageal cancer, or lung cancer.

The invention will be further described in the following examples, which do not limit the scope of the invention described in the claims.

EXAMPLES

Example 1—Identification of a Potent Class I MHC Molecule Epitope of a HER2/Neu Polypeptide HER-2/neu is a polypeptide that is overexpressed in a wide variety of cancers and is a therapeutic target, particularly in breast cancer. For example, NeuVax is a previously developed vaccine that includes the HER-2/neu-derived polypeptide p369-377 (amino acid sequence: KIFGSLAFL (SEQ ID NO:2), also called E75) derived from the extracellular domain of HER-2/neu and mixed with GM-CSF. This vaccine aims to prime the immune response against E75 so that T cells are generated that can recognize and kill the patient's cancer cells, which are presumably displaying the same peptides on their cell surface in association with MHC class I molecules.

Figure 1A:
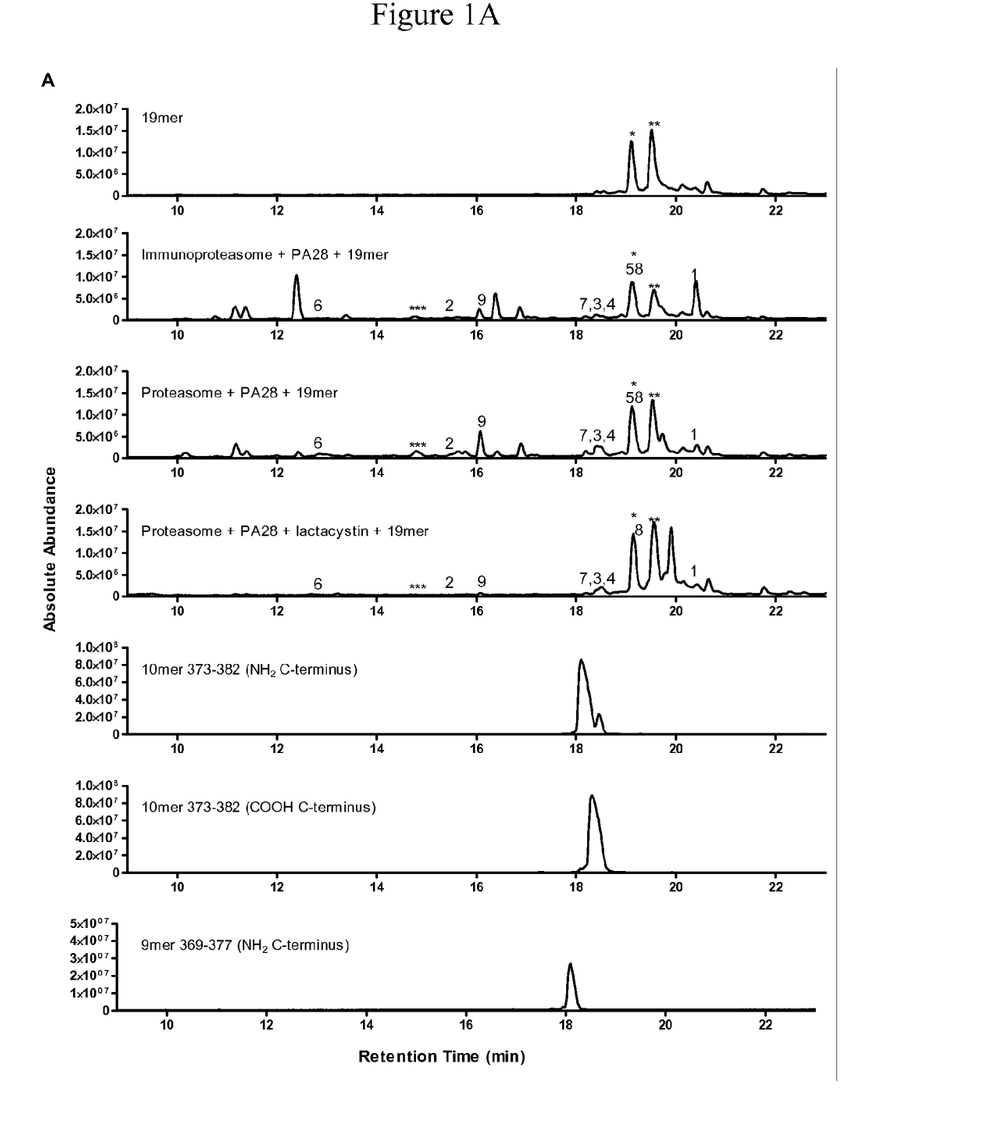
FIG. 1A shows example total ion chromatograms identifying polypeptides derived from HER-2/neu 19-mer polypeptide (FAGCKKIFGSLAFLPESFD) by proteasomal or immunoproteasomal catalysis.
Figure 1B:
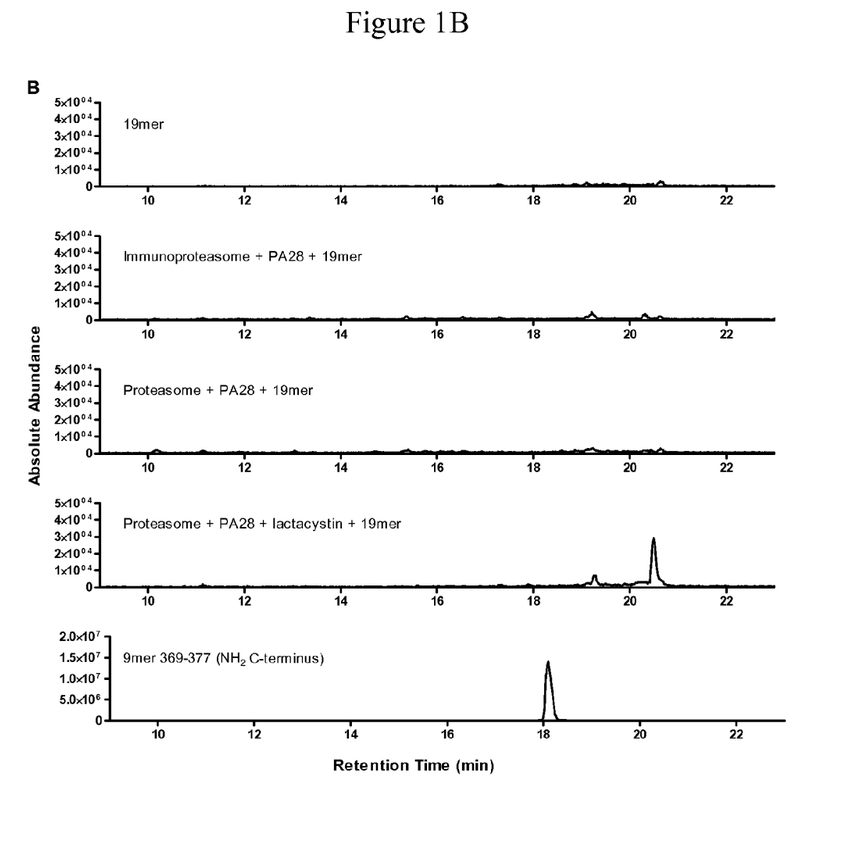
FIG. 1B shows example extracted ion chromatograms from the reactions described in FIG. 1A examining processing of HER-2/neu p369-377 from the 19-mer polypeptide.

The following was performed to determine if E75 is processed from HER-2/neu or HER-2/neu fragments by multi-subunit enzymes referred to as the proteasome and immunoproteasome, which are required for loading of polypeptide onto MHC class I molecules. To determine this, the 19-mer polypeptide, FAGCK<u>KIFGSLAFL</u>PESFD (SEQ ID NO:3), was synthesized. This polypeptide matches HER-2/neu amino acids 364-382, and it fully contains E75 (underlined). The 19-mer was then cleaved using purified 20S proteasome and immunoproteasome. Although E75 is reported to be cleaved as determined by proteasome algorithms, the in vitro data presented herein did not reveal processing of this polypeptide from longer HER-2/neu polypeptides (FIGS. 1A and 1B). However, the 19-mer polypeptide was consistently found to be processed into several other shorter polypeptides (FIG. 1A and Table 1). None of these shorter polypeptides scored as highly as E75 for binding to HLA-A2 using the mathematical algorithms (Table 1).

TABLE 1

| FIG. 1A label | HER-2/neu amino acid number | retention time (min) | Peptide | Peptide generated by immunoproteasome | Peptide generated by proteasome | (SYFPEITHI) HLA-A*0201 binding score | Cleavage predicted by ip/p servers |
|---|---|---|---|---|---|---|---|
| 1 | 371-381 | 20.4 | FGSLAFLPESF (SEQ ID NO: 4) | + | + | NA | Y |
| 2 | 364-374 | 15.45 | FAGCKKIFGSL (SEQ ID NO: 5) | + | + | NA | Y |
| 3 | 372-382 | 18.4 | GSLAFLPESFD (SEQ ID NO: 6) | + | + | NA | Y |
| 4 | 373-382 | 18.5 | SLAFLPESFD (SEQ ID NO: 1) | + | + | 13 | N |
| 5 | 371-380 | 19.1 | FGSLAFLPES (SEQ ID NO: 7) | + | + | 8 | N |
| 5 | 372-381 | 19.1 | GSLAFLPESF (SEQ ID NO: 8) | + | + | 5 | Y |
| 6 | 364-373 | 12.8 | FAGCKKIFGS (SEQ ID NO: 9) | + | + | 10 | N |
| 7 | 374-382 | 18.2 | LAFLPESFD (SEQ ID NO: 10) | + | + | 8 | N |
| 8 | 373-381 | 19.2 | SLAFLPESF (SEQ ID NO: 11) | + | + | 16 | N |
|  | 369-377 | NA | KIFGSLAFL (SEQ ID NO: 2) | − | − | 28 | Y |
| 9 | 375-382 | 16.06 | AFLPESFD (SEQ ID NO: 12) | + | + | NA | Y |
| * | 364-382 | 19.14 | FAGCKKIFGSLAFLPESFD-NH2 (SEQ ID NO: 13) | NA | NA | NA | NA |

TABLE 1-continued

| FIG. 1A label | HER-2/neu amino acid number | retention time (min) | Peptide | Peptide generated by immuno-proteasome | Peptide generated by pro-teasome | (SYFPEITHI) HLA-A*0201 binding score | Cleavage predicted by ip/p servers |
|---|---|---|---|---|---|---|---|
| * | 364-382 | 19.14 | FAGCKKIFGSLAFLPESFD-COOH (SEQ ID NO: 14) | NA | NA | NA | NA |
| ** | NA | 19.54 | FAGKKIFGSLAFLPESFD-NH2 (SEQ ID NO: 15) | NA | NA | NA | NA |
| ** | NA | 19.54 | FAGKKIFGSLAFLPESFD-COOH (SEQ ID NO: 16) | NA | NA | NA | NA |
| *** | NA | 14.78 | FAGKKIFGSL (SEQ ID NO: 17) | NA | NA | NA | NA |
| *** | NA | 14.78 | GKKIFGSLAF (SEQ ID NO: 18) | NA | NA | NA | NA |

A 19 mer sequence from HER-2/neu is processed into smaller polypeptide fragments by the immunoproteasome and proteasome, and these fragments are predicted to bind HLA-A*0201. The symbol (+) indicates the polypeptide was produced by the respective enzyme in an in vitro assay. The symbol (-) indicates lack of peptide detection in an in vitro assay in samples # containing the respective enzyme. The SYFPEITHI server was used to predict nonamer and decamer polypeptide binding to HLA-A*0201. The 20S and C-term 3.0 prediction methods on the Netchop 3.1 server and the Proteasome Cleavage Prediction Server with models 1, 2, and 3 for the proteasome and immunoproteasome enzymes were used to predict whether the smaller # polypeptide could be processed by the enzymes from the larger 19 mer sequence, irrespective of in vitro data. NA, not applicable, indicates that the polypeptide is either a deletion product, is starting material and thus would not be generated in the assay, or is too large for binding predictions to HLA- A*0201. Numbers and asterisks indicate peptide # labels in FIG 1A.

Figure 1C:
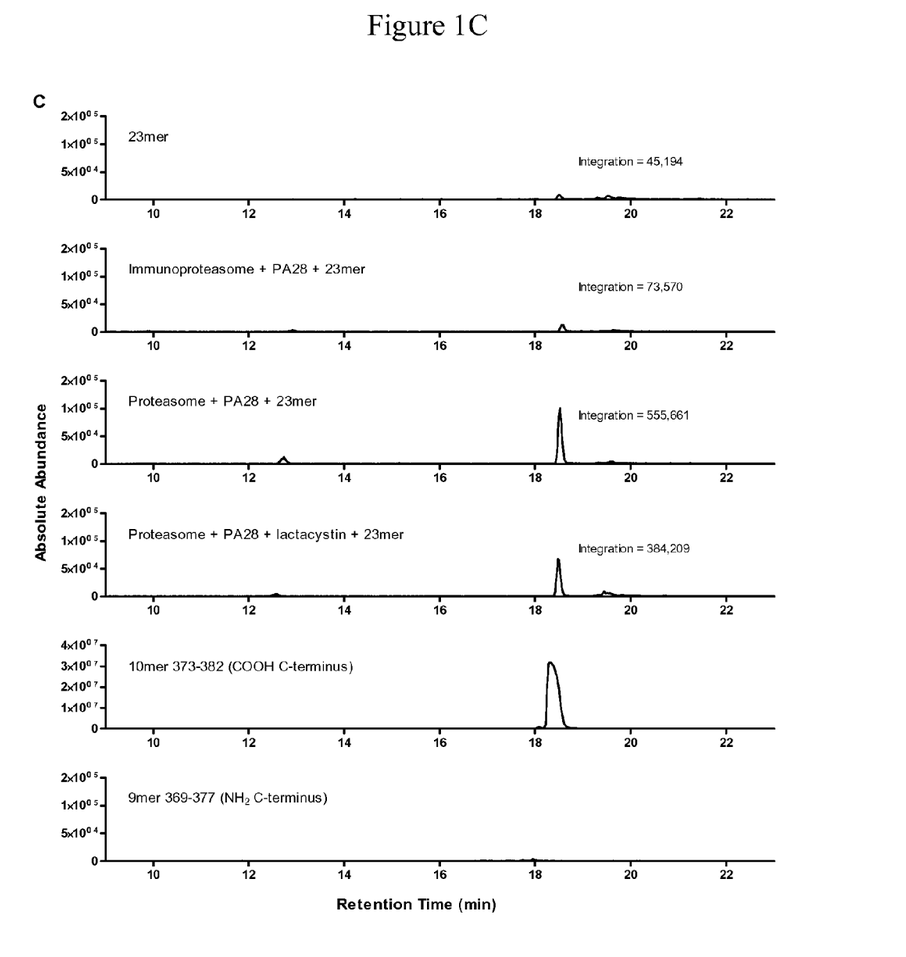
FIG. 1C shows example extracted ion chromatograms demonstrating that p373-382 (SLAFLPESFD) is processed from a HER-2/neu-derived 23-mer (QEFAGCKKIFGSLAFLPESFDGD; SEQ ID NO:19) by proteasomal or immunoproteasomal catalysis.

One of the observed processed polypeptides (p373-382) represented the end terminal ten amino acids of the 19-mer. To determine if this polypeptide could be processed from larger peptides, a 23-mer containing p373-382 was synthesized and treated with the proteasomes. As shown in FIG. 1C, p373-382 was indeed released from the 23-mer.

Figure 2:
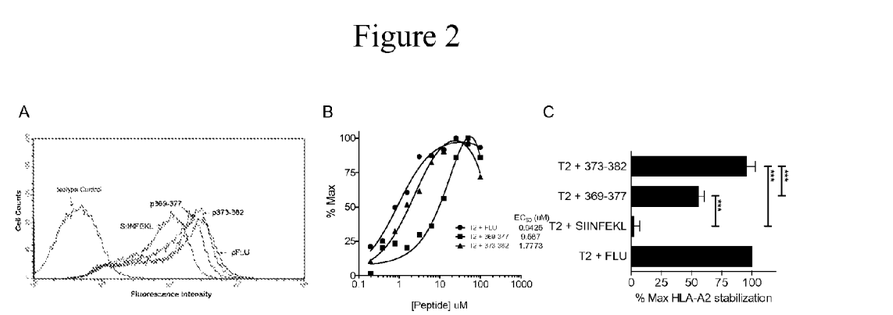
FIG. 2A shows HER-2/neu polypeptide p373-382 binding to TAP deficient T2 cells.
FIG. 2B shows dose dependent saturable binding of HER-2/neu polypeptide p373-382 to T2 cells.
FIG. 2C shows relative binding affinities of HER-2/neu polypeptide p373-382 and p369-377 compared to high affinity influenza-derived HLA-A2 binding polypeptide, GILGFVFTL (p58-66; SEQ ID NO:20).

Many of the polypeptides that were processed in the assay were synthesized and tested for binding to the class I MHC molecule, HLA-A2, using the standard T2 HLA-A2 stabilization assay. HLA-A2 is an MHC class I molecule that is prevalent in approximately 30-40% of the Caucasian population. It is often used as a target in vaccine trials since it has the potential to benefit a large number of breast cancer patients. One of the synthesized polypeptides, p373-382 (SLAFLPESFD), was able to strongly bind the HLA-A2 molecule, at levels comparable to the positive control, a polypeptide from the influenza virus (FLU) (FIG. 2). Surprisingly, even low levels of p373-382 bound, compared to p369-377, which required higher concentrations (FIG. 2).

Taken together, these results demonstrate that the HER-2/neu polypeptide p373-382 is processed from longer HER-2/neu polypeptides and binds HLA-A2.

An ELIspot was performed to determine if the p373-382 epitope is naturally processed by the cellular machinery in cancer cells and to determine if it has the potential of being bound to HLA-A2 on the surface of cancer cells, where it can serve as a target for primed and activated immune cells. If specific immune cells can recognize the p373-382:HLA-class I complex on cancer cells, then they can kill the cancer cells and prevent the cancer from progressing in patients. Since it was shown that the p373-382 polypeptide was processed in vitro by cellular machinery and was capable of binding strongly to HLA-A2 molecules, an ELIspot was performed to determine whether CD8+ T cells generated using the p373-382 polypeptide can be generated and if these T cells are able to recognize HER-2/neu+ breast cancer cells.

FIG. 3A reveals that that CD8+ T cell lines were generated using the pFLU polypeptide (control), p369-377, and p373-382. The control FLU T cells only recognized target cells pulsed with FLU polypeptide, as expected. HER-2/neu p369-377 polypeptide-generated T cells recognized target cells pulsed with p369-377 polypeptide and target cells pulsed with p373-382. p373-382-generated T cells recognized target cells pulsed with either the p373-382 polypeptide or the p369-377 polypeptide, indicating that there is cross-reactivity between the two polypeptides which could be due to the fact that they share five amino acids.

Next, the generated T cell lines were assessed in an in vitro ELISPOT assay to determine whether they could recognize a panel of breast cancer cell lines that express varying levels of HER-2/neu at their surface. In all cases, the p373-382-generated CD8+ T cells were able to recognize the breast cancer cells at much higher levels compared to the p369-377-generated CD8+ T cells and the control FLU CD8+ T cells (FIG. 3B). BT20 cells express HER-2/neu, but do not express HLA-A2 and thus served as a negative control. These results indicate that breast cancer cells express p373-382 on their surface in the context of HLA-A2 and that CD8+ T cells generated using p373-382 have the ability to recognize these cancer cells.

Another in vitro assay was performed to measure lysis of the breast cancer cells by the T cells. Again, the CD8+ T cells generated using the p373-382 polypeptide recognized and lysed all tested breast cancer cell lines at much higher levels compared to the CD8+ T cells generated using the p369-377 polypeptide (FIG. 3C). In this assay, BT20 cells were a negative control as well as the FLO cells, which express HLA-A2, but do not express HER-2/neu.

Figure 3:
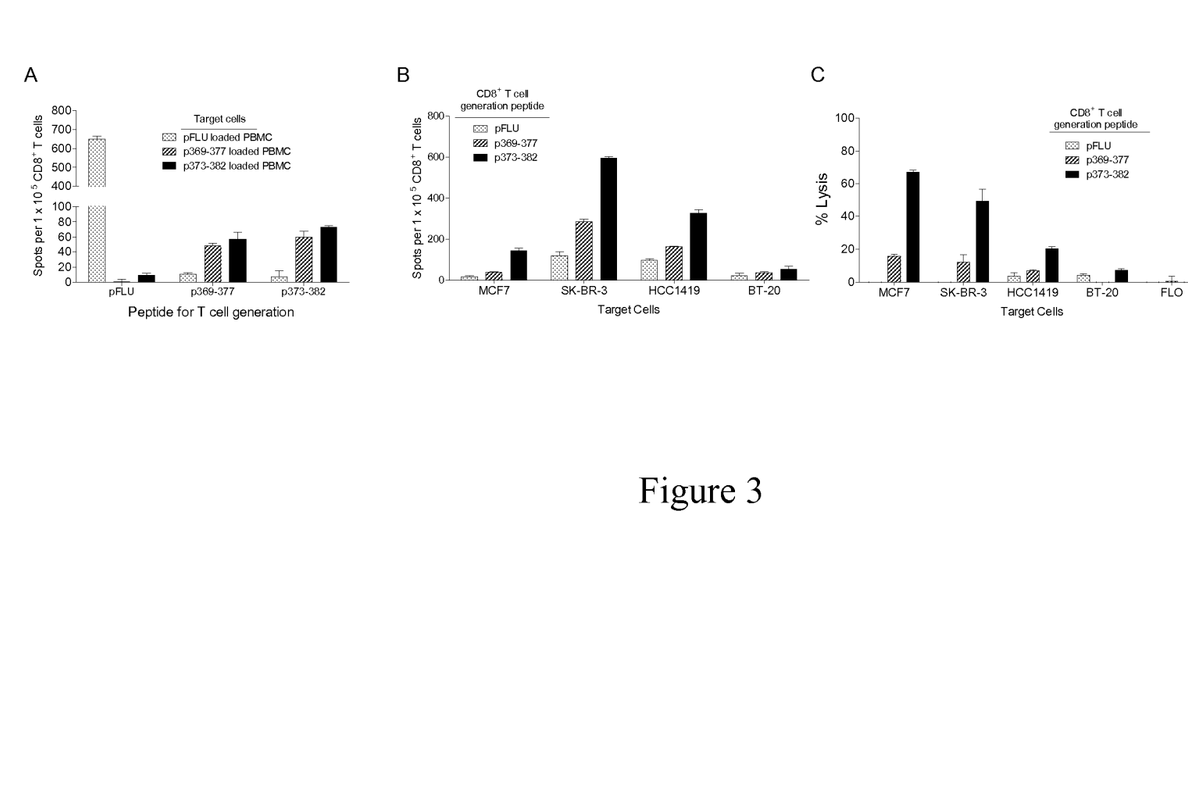
FIG. 3A shows IFN-γ ELIspot analysis showing that CD8 T cells generated against HER-2/neu polypeptide p373-382 respond to autologous cells loaded with either p373-382 or p369-377.
FIG. 3B shows IFN-γ ELIspot analysis demonstrating that CD8 T cells generated against HER-2/neu polypeptide p373-382 respond to HER-2/neu-expressing tumor cells with release of IFN-γ.
FIG. 3C shows cytotoxic T cell analysis demonstrating that CD8 T cells generated against HER-2/neu polypeptide p373-382 lyse HER-2/neu-expressing tumor cells.
Figure 4:
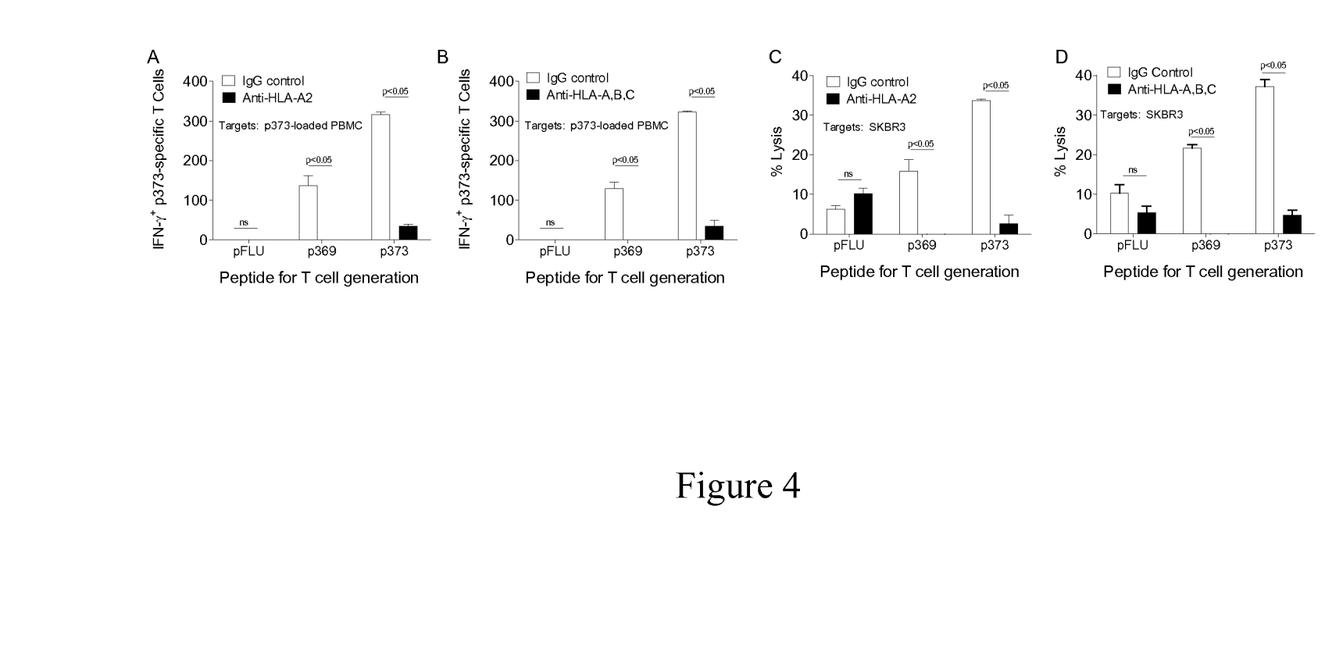
FIGS. 4A-B shows, using IFN-γ ELIspot analysis, that the IFN-γ response of CD8 T cells generated against HER-2/neu polypeptide p373-382 is blocked by MHC class I blocking antibodies (FIG. 4A: anti-HLA-A2.
FIGS. 4C-D shows, using cytotoxic T cell assays, that the lysis response of CD8 T cells generated against HER-2/neu polypeptide p373-382 is blocked by MHC class I blocking antibodies (FIG. 4C: anti-HLA-A2.

Lastly, in order to confirm that the p3737-382 polypeptide was activating CD8 T cells in an HLA restricted manner, T cell lines generated with the three polypeptides used in FIG. 3 were assayed for peptide-specific reactivity or lytic activity in the presence of neutralizing HLA-A2 or HLA-ABC monoclonal antibodies. As shown in FIG. 4A-B, the reactivity, as assessed by IFN-γ release, of the p373-382-generated T cells was markedly suppressed by inclusion of either antibody as compared to T cells treated with control isotyped matched antibody. In parallel, it also was observed that neutralizing HLA-A2 or HLA-ABC monoclonal antibodies blocked lysis of tumor cells by p373-382-generated T cells as shown in FIGS. 4C-D, respectively.

The findings described in the preceding three paragraphs were repeated two to four times using T cells generated from two to three HLA-A2+ donors.

Algorithms were used to determine the potential for other HLA alleles, in addition to HLA-A2, to bind to p373-382 or some other embedded polypeptide. The algorithms used were SYPEITHI and NetMHCpan. The results of this investigation suggest that p373-382 or some fragments may bind other HLA class molecules (Table 2).

TABLE 2

Epitopes predicted within p373-382

| HLA Polymorphism | Octamers | Nonamers | Decamers |
|---|---|---|---|
| HLA-A*0201 | — | — | SLAFLPESFD |
| HLA-A*03 | — | — | SLAFLPESFD |
| HLA-A*1101 | — | — | SLAFLPESFD |
| HLA-A*2402 | — | SLAFLPESF | — |
| HLA-A*26 | — | SLAFLPESF | — |
| HLA-B*08 | LAFLPESF (SEQ ID NO: 21) | SLAFLPESF | — |
| HLA-B*14 | — | SLAFLPESF | — |
| HLA-B*1501 | — | SLAFLPESF | SLAFLPESFD |
| HLA-B*18 | SLAFLPES (SEQ ID NO: 22) | SLAFLPESF | — |
| HLA-B*2705 | — | SLAFLPESF | — |
| HLA-B*37 | LAFLPESF | SLAFLPESF | — |
| HLA-B*4402 | — | SLAFLPESF | — |
| HLA-B*5101 | LAFLPESF | LAFLPESFD | — |
| HLA-C*01041 | LAFLPESF | — | — |

Algorithm: SYFPEITHI [world wide web at "syfpeithi.de/"], Threshold Score: 10
Algorithm: NetMHCpan [world wide web at "cbs.dtu.dk/"], Threshold 5%
— None Taken together, the results provided herein demonstrate that p373-382 (SLAFLPESFD) serves as a prime candidate for cancer vaccines and therapeutics for HER-2/neu patients. p373-382 is processed in vitro by cellular enzymes, and it binds a prevalent MHC class I molecule, HLA-A2. CD8+ T cells from human blood can be generated against this polypeptide, and these T cells can recognize breast cancer cells, indicating that breast cancer cells are naturally processing p373-382 from the expressed HER-2/neu polypeptide and presenting p373-382 on the cell surface in the context of HLA-A*0201.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a polypeptide, wherein the sequence of said polypeptide consists of the amino acid sequence set forth in SEQ ID NO:1, wherein said polypeptide is immunogenic, and wherein said composition comprises an adjuvant and an agent selected from the group consisting of IL-2, GM-CSF, and rintatolimod.

2. The composition of claim 1, wherein said adjuvant is an oil and water mixture.

3. The composition of claim 1, wherein said adjuvant is Montanide ISA-51.

4. The composition of claim 1, wherein said agent is IL-2.

5. A method for increasing the number of $CD8^+$ T cells having the ability to kill breast cancer cells expressing a HER2/neu polypeptide, wherein said method comprises contacting a population of $CD8^+$ T cells with a polypeptide and an agent selected from the group consisting of IL-2, GM-CSF, and rintatolimod, wherein the sequence of said polypeptide consists of the amino acid sequence set forth in SEQ ID NO:1.

6. The method of claim 5, wherein said contacting step occurs in an ex vivo manner.

7. The method of claim 5, wherein said contacting step occurs in an in vivo manner.

8. A method for increasing, within a human, the number of CD8⁺ T cells having the ability to kill breast cancer cells expressing a HER2/neu polypeptide, wherein said method comprises administering a composition to said human, wherein said composition comprises a polypeptide and an agent selected from the group consisting of IL-2, GM-CSF, and rintatolimod, wherein the sequence of said polypeptide consists of the amino acid sequence set forth in SEQ ID NO:1.

9. The method of claim 8, wherein said human contains breast cancer cells expressing said HER2/neu polypeptide.

10. The method of claim 8, wherein said composition comprises an adjuvant.

11. The method of claim 10, wherein said adjuvant is an oil and water mixture.

12. The method of claim 10, wherein said adjuvant is Montanide ISA-51.

13. The method of claim 8, wherein said agent is IL-2.

14. The method of claim 8, wherein said agent is GM-CSF.

15. The method of claim 8, wherein said method further comprises administering trastuzumab to said human.

\* \* \* \* \*